(12) United States Patent
Cartner et al.

(10) Patent No.: US 8,823,525 B2
(45) Date of Patent: *Sep. 2, 2014

(54) HYGIENE COMPLIANCE MONITORING SYSTEM

(75) Inventors: Todd J. Cartner, Uniontown, OH (US); Jackson W. Wegelin, Stow, OH (US)

(73) Assignee: GOJO Industries, Inc., Akron, OH (US)

(*) Notice: Subject to any disclaimer, the term of this patent is extended or adjusted under 35 U.S.C. 154(b) by 570 days.

This patent is subject to a terminal disclaimer.

(21) Appl. No.: 12/987,389

(22) Filed: Jan. 10, 2011

(65) Prior Publication Data

US 2011/0169645 A1 Jul. 14, 2011

Related U.S. Application Data

(63) Continuation-in-part of application No. 12/685,110, filed on Jan. 11, 2010, now Pat. No. 8,717,177.

(51) Int. Cl.
*G08B 23/00* (2006.01)
*G06F 19/00* (2011.01)

(52) U.S. Cl.
CPC .......... *G06F 19/327* (2013.01); *G06F 19/3493* (2013.01)
USPC ........... 340/573.1; 340/517; 340/523; 222/52

(58) Field of Classification Search
USPC ........ 340/573.1, 573.4, 540, 541, 567, 539.1, 340/539.11, 539.12, 517, 523, 526; 4/39, 4/52, 222, 223; 422/26, 28, 123, 124; 700/236, 238; 222/39, 52, 222, 223
See application file for complete search history.

(56) References Cited

U.S. PATENT DOCUMENTS

| | | | |
|---|---|---|---|
| 4,258,354 A | 3/1981 | Carmon et al. | |
| 5,900,801 A | 5/1999 | Heagle et al. | |
| 5,939,974 A | 8/1999 | Heagle et al. | |
| 6,236,317 B1 | 5/2001 | Cohen et al. | |
| 6,542,568 B1 * | 4/2003 | Howes et al. | 377/16 |
| 2003/0149979 A1 * | 8/2003 | Baldwin et al. | 725/39 |
| 2008/0049756 A1 * | 2/2008 | Suzuki | 370/395.1 |
| 2010/0332022 A1 * | 12/2010 | Wegelin et al. | 700/231 |
| 2011/0126223 A1 * | 5/2011 | Shahraray et al. | 725/28 |

FOREIGN PATENT DOCUMENTS

| | | |
|---|---|---|
| WO | 03082351 A2 | 10/2003 |
| WO | 2004064959 A1 | 8/2004 |
| WO | 2006135922 A2 | 12/2006 |

* cited by examiner

*Primary Examiner* — Hoi Lau
(74) *Attorney, Agent, or Firm* — Renner, Kenner, Greive, Bobak, Taylor & Weber

(57) ABSTRACT

An electronic hand hygiene compliance system and award indicator that provides realtime reporting of the percent number of hand hygiene events against a programmed target number of hand hygiene events for a given functional area over a given period of time, yielding hand hygiene compliance. The system keeps up to date compliance for an established group interval until the data is written over by compliance data for the same group interval the following day. In addition, a random hand hygiene event can be identified for a given functional area during a given period of time to trigger an alarm for encouraging hand hygiene activity for a given dispenser or group of dispensers.

25 Claims, 12 Drawing Sheets

HYGIENE COMPLIANCE MONITORING SYSTEM

CROSS-REFERENCE TO RELATED APPLICATION

This application is a continuation-in-part of U.S. patent application Ser. No. 12/685,110 filed on Jan. 11, 2010, now U.S. Pat. No. 8,717,177 the contents of which are incorporated herein by reference.

TECHNICAL FIELD

The present invention generally relates to systems to monitor hand hygiene. Particularly, the present invention relates to compliance monitoring systems that utilize an electronic hand hygiene compliance gauge that records and totals hand hygiene events at a single location or combined as a functional grouping (multiple locations) and reports them against a target number of hand hygiene events for a given period of time. The present invention may also utilize an award indicator that is triggered at a random hand hygiene event during a programmed period of time.

BACKGROUND OF THE INVENTION

Recently, the public has become increasingly concerned with disease and its transmission, and as such, there is an increased awareness of the importance of cleansing and hygiene in general. For example, with respect to the transmission of *E. coli* in the food services industry, the rhinovirus in elementary schools, and nosocomial diseases within healthcare facilities, numerous studies have cited hand hygiene as an effective measure to guard against disease transmission. Moreover, the Center for Disease Control (CDC) has set forth that hand washing and sanitizing is the single most important factor in the prevention of disease and the spread of infection. In response, the health care industry, the food services industry, and the hotel and travel industries have been forced to examine their protocols and procedures to ensure that their personnel are adopting hand cleansing habits that are efficacious in the prevention of disease transmission.

In order to minimize the chance of the transmission of bacteria or viruses by hand washing, full compliance with hand washing hygiene standards must be observed, as the failure of one individual to properly sanitize his or her hands can negate the efforts of others who come in contact with such individual. Thus, to ensure that full compliance occurs, many industries have trained individuals who are charged with overseeing compliance with hygiene standards. Unfortunately, individuals overseeing compliance with hygiene standards typically have other responsibilities, which often interfere with their ability to effectively monitor hygiene compliance. To overcome this, automated systems have been proposed to monitor the usage habits of soap and sanitizer dispensers as an aid in the determination of whether compliance with hygiene protocols is being achieved. However, due to the relatively complex nature of these systems, trained individuals are generally needed to administrate and maintain the systems. Additionally, because individuals responsible for overseeing the operation of the compliance monitoring systems are often subject to high turnover, frequent retraining is necessitated, which requires substantial time and expense.

Thus, current hygiene compliance monitoring systems typically do not offer robust data collection features and are generally too complex to install, administrate, and maintain to be utilized on a large scale in environments where the monitoring and assessment of compliance with hygiene standards is of critical importance and benefit to prevent disease transmission.

Therefore, there is a need for a user-friendly hygiene compliance monitoring system for assessing compliance with predetermined hygiene protocols. In addition, there is a need for a hygiene compliance monitoring system to monitor the use of soap and sanitizer dispensers that collect hygiene usage data in time segments or shift time intervals. Furthermore, there is a need for a hygiene compliance monitoring system that is low-cost and can provide information that is maintained confidentially and for a limited duration. There is also a need for a hygiene compliance system that can provide an award indicator based on the same shift time intervals to which compliance is monitored. There is also a need for a versatile hygiene compliance system and award indicator that allows for different modes and displays to be set by an administrator.

SUMMARY OF THE INVENTION

In light of the foregoing, it is a first aspect of the present invention to provide a hygiene compliance monitoring system for a dispenser maintaining material to be dispensed. The hygiene compliance monitoring system includes a controller having at least one shift time interval and a target value of hand hygiene events corresponding to at least one shift time interval. The system includes an activation switch that communicates hand hygiene event data to a memory unit. The memory unit includes at least one memory bank, which corresponds to the shift time interval. The controller compares the hand hygiene event data to the target value of hand hygiene events.

It is another aspect of the present invention to provide a hygiene compliance monitoring system for a functional grouping of dispensers. The functional grouping of dispensers includes more than one dispenser maintaining material to be dispensed. The hygiene compliance monitor includes a dispenser controller that is coupled to an actuator of each dispenser within the functional grouping of dispensers. The actuator initiates the dispensation of material from the dispenser when actuated, and the controller is programmed with a target value of hand hygiene events. The system further includes a data transmission unit adapted to be coupled to the dispenser controller of each dispenser within the functional grouping of dispensers. The data transmission unit includes a data collection memory unit and an internal clock in synchronization with the other dispensers of the functional grouping of dispensers. The memory unit includes at least one memory bank for receiving data and the data transmission unit generates a series of successive shift time intervals wherein the shift time intervals are periods to which at least one memory bank stores data from the internal clock. The shift time intervals of the system are repeated in a sequence, and each memory bank is deleted at the start of each shift time interval. The system further includes at least one data acquisition unit configured to set the clock and being further configured to receive at least one piece of data of from actuation.

Yet another aspect of the present invention is to provide a method of hygiene compliance monitoring, including the steps of providing a data transmission unit maintained by a dispenser, the dispenser including an actuator to initiate the dispensation of material from a refill container and a plurality of memory banks. The data transmission unit performs the steps of storing a target value of dispensations, generating a plurality of shift time intervals of a predetermined duration that repeat in a sequence, wherein each shift time interval corresponds to each memory bank; clearing the memory bank at the beginning of each shift time interval; monitoring the engagement of the actuator; and storing the number of engagements for shift time interval into each memory bank; and providing a data acquisition unit having a display and keypad. The data acquisition unit is configured to communicate with the data transmission unit, and the data transmission unit transfers the number of engagements and associated shift time intervals to the display of the data acquisition unit.

Yet another aspect of the present invention is to a method of hygiene compliance monitoring including the steps of providing a plurality of data transmission units each maintained by a dispenser. The dispenser includes an actuator to initiate the dispensation of material from a refill container and a plurality of memory banks. The data transmission unit stores a target value of dispensations, generates a plurality of shift time intervals of a predetermined duration that repeat in a sequence, wherein each said shift time interval corresponds to each said memory bank, clears the memory bank at the beginning of each said shift time interval, monitors the engagement of the actuator, and stores the number of engagements for each shift time interval into each memory bank. The method further includes the steps of providing a data acquisition unit having a display and keypad. The data acquisition unit is configured to communicate with the data transmission unit, and wherein the data transmission unit transfers the number of engagements and associated shift time intervals to the display of the data acquisition unit.

Yet another aspect of the present invention is to a hygiene compliance monitor for a functional grouping of dispensers maintaining material to be dispensed. The hygiene compliance monitor includes a dispenser controller that is coupled to an actuator of each dispenser to initiate the dispensation of material from the dispenser when the actuator is actuated. Each dispenser includes a data transmission unit adapted to be coupled to the dispenser controller. The data transmission unit includes a data collection memory unit and an internal clock in synchronization with the other dispensers. The memory unit has more than one memory bank for receiving data. The data transmission unit generates a series of successive shift time intervals that are periods to which the memory banks store data from the internal clock. The shift time intervals are repeated in a sequence, and each memory bank is deleted at the start of each shift time interval. The monitor further includes at least one data acquisition unit configured to set the clock and to receive at least one piece of data from actuation. The data is then compared to a target value of hand hygiene events.

In still another aspect of the present invention a dispenser monitoring unit to monitor hand hygiene compliance of at least one dispenser that transmits a hand hygiene event each time an actuator is engaged to dispense material therefrom comprises a monitoring controller. The dispenser monitoring unit also includes a monitoring transceiver that is coupled to the monitoring controller that receives hand hygiene events transmitted from the at least one dispenser. A data collection memory unit and an internal clock are each coupled to the monitoring controller, with the memory unit having at least one memory bank for receiving at least one hand hygiene event, the monitoring controller generates a series of successive shift time intervals, wherein the shift time intervals are periods to which the at least one memory bank stores data from the internal clock, the shift time intervals being repeated in a sequence, and each of the at least one memory bank is deleted at the start of each shift time interval.

BRIEF DESCRIPTION OF THE DRAWINGS

These and other features and advantages of the present invention will become better understood with regard to the following description, appended claims, and accompanying drawings where:

BEST MODES FOR CARRYING OUT THE INVENTION

It is known in the art that hand hygiene compliance is typically calculated as the ratio of the number of actual hand hygiene events to the number of hand hygiene events that should have occurred. Thus, to facilitate the determination of whether hygiene compliance standards are being followed, the system of the present invention generally monitors hand hygiene events that have actually occurred, which may be used in conjunction with data related to the number of hand hygiene events that should have occurred to establish a measure of hand hygiene compliance.

Figure 1:
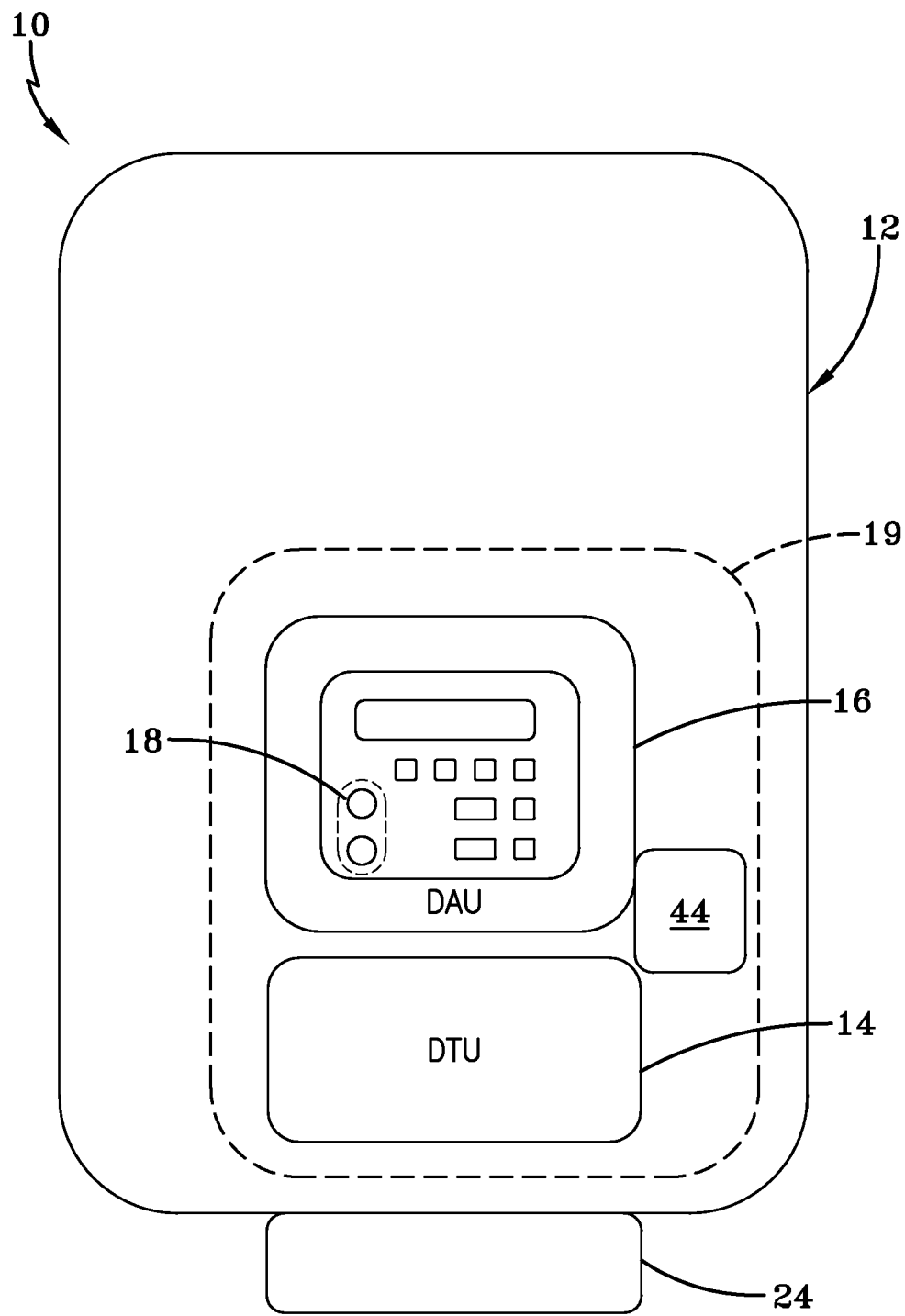
FIG. 1 is a block diagram of a self-contained hygiene compliance monitoring system that provides a data transmission unit maintained at a dispenser, which transmits hygiene compliance data to a data acquisition unit in accordance with the concepts of the present invention.

A certain embodiment of a hygiene compliance monitoring system is generally referred to by the numeral 10, as shown in FIG. 1 of the drawings. The hygiene compliance monitoring system 10 is generally used in connection with a dispenser 12, such as a dispenser that dispenses material, such as soap, sanitizer, moisturizer, and the like. However, it should be appreciated that the hygiene compliance monitoring system 10 may be used in association with dispensers used to dispense any suitable material or item. In order to carry out the functions of the hygiene compliance monitoring system 10, a data transmission unit (DTU) 14 is associated with the dispenser 12 to collect hygiene data or events, which may include the number of shots of soap dispensed by the dispenser 12 or the number of hand hygiene events occurring at the dispenser 12, such that a hand hygiene event may include one or more shots of soap dispensed by the dispenser 12 within a certain dwell time, or period of time, such as three seconds for example, as it is known that on occasion a user will activate the dispenser 12 to provide two or more shots of soap in a consecutive fashion during a single hand hygiene event. It should also be appreciated that any other desired data associated with the operation of the dispenser 12 can be collected by the DTU 14 as well.

The data sent by the data transmission unit 14 is then transmitted to a data acquisition unit (DAU) 16, which is positioned on the face of the dispenser 12. As such, as later discussed, the data may be stored on the DAU 16 in a manner so that it can be later used as a basis for reporting hand hygiene compliance and signaling an award indicator 18. Preferably, the DAU 16 and DTU 14 are incorporated within a single module 19, which may be easily incorporated to a new dispenser or retrofitted to an existing dispenser. Thus, the hygiene compliance system 10 provides a convenient and user-friendly system which may be used to collect data relating to the use of the dispenser 12, so as to assist in determining whether predetermined hygiene standards and protocols are being achieved. Such hygiene compliance can include, but is not limited to daily and shift compliance.

Figure 2:
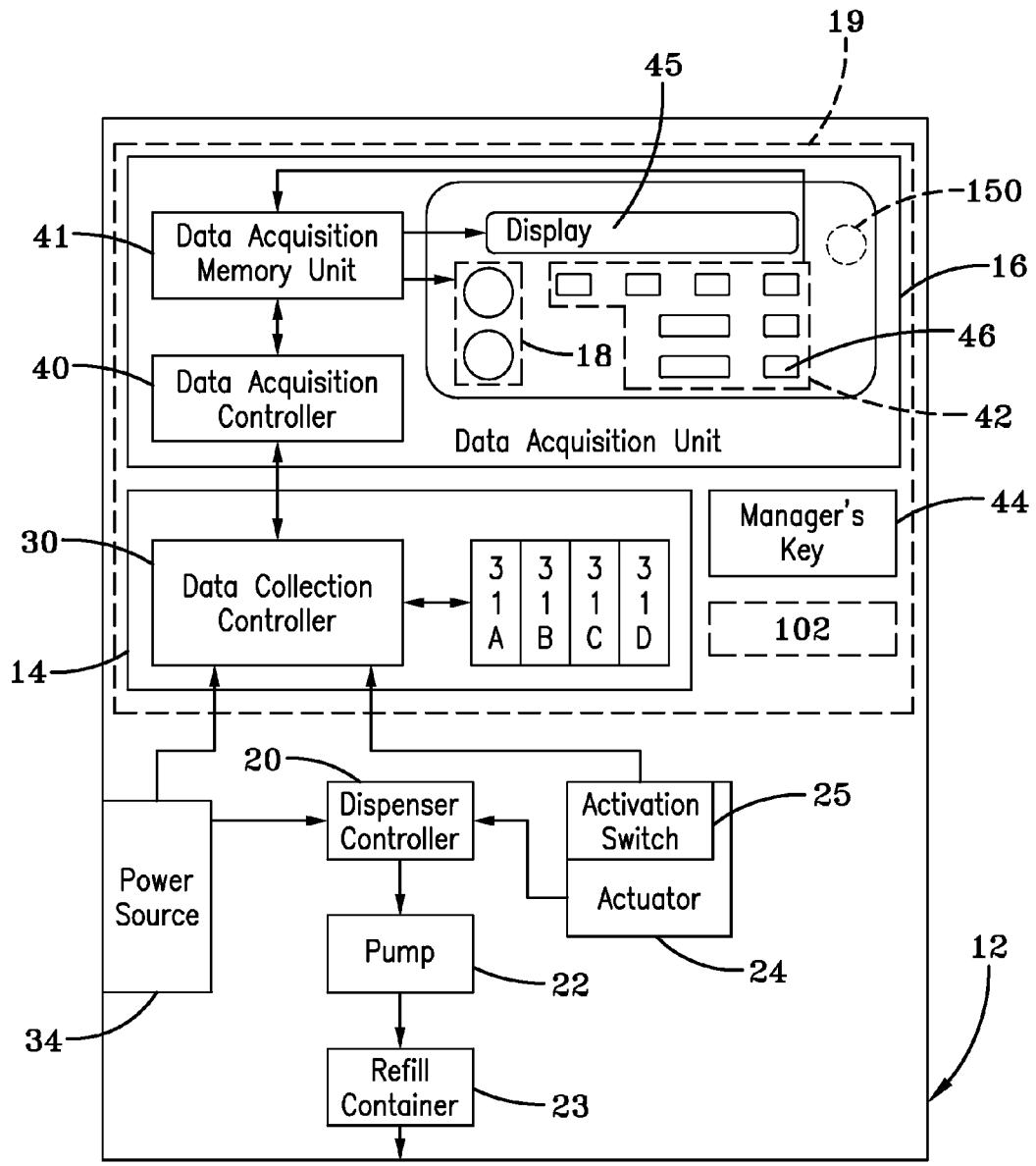
FIG. 2 is a block diagram of the data transmission unit and data acquisition unit associated with the dispenser in accordance with the concepts of the present invention.

Continuing to FIG. 2, in various embodiments of the invention, the dispenser 12 maintains a dispenser controller 20, which controls a pump 22 connected thereto. A refill container 23 is operatively coupled to the pump 22 and may maintain any desired material, such as soap, sanitizer, moisturizer, or the like. Also coupled to the controller 20 is an actuator 24 that when engaged or otherwise actuated, commands the dispenser controller 20 to actuate the pump 22, so as to dispense material from the refill container 23. In one aspect, the actuator 24 may comprise a proximity sensor or other device that is actuated upon the detection of the presence of a user's hand. However, in further aspects of the invention, the actuator may be coupled to a manual push bar wherein material is dispensed onto the user's hand when the user manually activates the push bar. The actuator includes an activation switch 25, which is used to communicate that a hand hygiene event occurred, as will be further discussed below.

The dispenser 12 also includes the data transmission unit 14, which is coupled to the dispenser controller 20. The data transmission unit 14 may be implemented in hardware, software, or a combination of both. In one aspect, the data transmission unit 14 may be integral with the dispenser controller 20 or maintained separately therefrom, as shown in FIG. 2. In yet another aspect, the data transmission unit 14 may be provided as a separate component that provides a compatible interface for communicating with the dispenser 12 to allow the data transmission unit 14 to be retrofit with the dispenser 12. Thus, the features provided by the hygiene compliance monitoring system 10 may be subsequently added or retrofitted to previously-installed dispensers 12 that lack such features.

The data transmission unit 14 maintains a data collection controller 30, which is coupled to the dispenser controller 20 of the dispenser 10. The data collection controller 30 includes the necessary hardware, software, or combination of both needed to carry out the functions to be discussed. Specifically, the data collection controller 30 maintains an event count or event count value, which is incremented based on the number of actuator 24 engagements that have been made to dispense material from the dispenser 12 during a particular shift time interval or time segment. The event count or event count value may be based on the actual number of dispenses from the dispenser, or the number of hand hygiene events, which may include a number of dispenses from the dispenser in a predetermined period of time, or both the actual number of dispenses and the number of hand hygiene events. Preferably, for each current shift time interval or time segment, the data collection controller 30 maintains an event count value that in certain embodiments is incremented each time a hand hygiene event occurs. And as such, it is the combination of the hand hygiene event count value and associated target value for the shift time interval which comprises the hygiene compliance data.

Coupled to the data collection controller 30 is a data collection memory unit 31 that stores data collected by the data transmission unit 14. Specifically, the data collection memory unit 31 of the data transmission unit 14 is configured such that the memory available for storing data is divided into time segments or shift time intervals of a predetermined duration. Preferably, the stored data is divided into four memory banks, 31A, 31B, 31C, and 31D that store data over four separate time segments or shift time intervals A, B, C, and D per day to establish a per day compliance analysis. The end of each shift time interval is the beginning of the following shift time interval. As such, once the duration of the time segments has been set via the data acquisition unit 16 in a manner to be discussed, the number of hand hygiene events that occur during each recurring time segment or shift time interval are recorded and stored at the data collection memory unit 31 until the information is written over at the start of the same shift time interval of the next day.

Setting the durational size of the time segment or shift time interval that is used to collect hygiene compliance data at the data transmission unit 14 and limiting the total number of shift time intervals or time segments to one day ensure that the data collection memory unit 31 is precise and not overrun. In addition, the manner in which the information is stored on a short-term basis provides confidentiality with respect to hand hygiene compliance.

Continuing, the memory unit 31 may preferably comprise non-volatile memory, such that hygiene compliance data collected and stored at the data collection memory unit 31 is not erased if power to the data transmission unit 14 is lost. Data acquired by the data transmission unit 14 is stored at the data collection memory unit 31 and is in communication with the data acquisition unit 16, which is coupled to the data collection controller 30. The data transmission unit 14, as well as the components of the dispenser 10, is powered by a power source 34, which may comprise a portable power source, such as a battery, or may comprise a mains power source that is plugged into a wall outlet. Alternatively, the data transmission unit 14 may provide its own power source, such as a rechargeable or replaceable battery, independently from that of the dispenser 12.

The data acquisition unit 16, which acquires the collected hygiene data from the data transmission unit 14, comprises a data acquisition controller 40 that includes the necessary hardware, software, or combination of both needed to provide the functions to be discussed. Alternatively, the data acquisition controller can be integrated within the data collection controller 30. In one aspect, the data acquisition controller 40 also maintains an internal clock to track the current time and day. In one aspect, the internal clock may be set via the DAU 16. The internal clock may also function such that time is traced in negative relation to the current time.

Also coupled to the data acquisition controller 40 is a data acquisition memory unit 41 that may comprise volatile memory, non-volatile memory, or a combination of both, which is used to carry out various functions to be discussed. It is also contemplated that the data acquisition unit 16 is configured to maintain a database at the data acquisition memory unit 41 of dispenser shift time interval data that is associated with dispenser 12 over a select period of time, as will be discussed with respect to award indicator 18.

Also coupled to the data acquisition controller 40 is a keypad 42 that allows the user to enter information and commands into the data acquisition unit 16. For example, the keypad 42 may comprise a combination of numeric and/or alphanumeric and/or arrow keys that allow a user to enter various system configuration codes to initiate commands at the data transmission unit 14, in a manner to be discussed. In addition, the keypad 42 may be used to enter commands to initiate and control various functions provided by the system 10. Other means of manipulating the data or controlling various functions provided by the data acquisition unit 16 are also foreseen, including the use of a touch screen, thumb wheel, as well as any other system for data entry or interaction with the data acquisition unit 16. In the preferred embodiment, it is contemplated that a manager's key 44 will be required to change any of the programmable features and settings. Manager's key 44 may consist of a wireless or mechanical mechanism known in the art, or a personal identification number (PIN) entered on the keypad.

In addition, the data acquisition unit 16 includes a display 45 which may comprise an LCD (liquid crystal display) display or the like and which allows the user to view the various commands and compliance data display modes. Examples of display modes that may be used, but are not necessarily limited to, are hand hygiene total events, hand hygiene compliance percentage, and no display.

Hand hygiene total events mode is the display that relates to the total number of hand hygiene events for the active period. In this mode, the total number is shown, and the user is not informed of the target number of hand hygiene events for the active period or shift. Hand hygiene compliance percentage mode is the current percentage of actual number of hand hygiene events over the target number of hand hygiene events for the current period or shift. The target number of hand hygiene events could either be set as a specific integer value or can be set as a function of time. No display mode may be utilized in order to eliminate the Hawthorne Effect, which is a form of reactivity whereby subjects alter or improve an aspect of their behavior being experimentally measured simply in response to the fact that they are being studied.

Furthermore, it should be appreciated that the read dispenser button 46 may be depressed in a predetermined sequence to enable one or more operating modes, including a read-shift time interval mode in which newly-collected event data for the current shift plus the previous three shifts, which is the latest data stored for each four manager configured and programmable shift time intervals; a read-all mode in which all compliance data collected by the data transmission unit 14 for the current shift time interval along with the prior three intervals; and a read/erase mode in which all data collected by the data transmission unit 14 is erased from the data collection memory unit 31.

Figure 3:
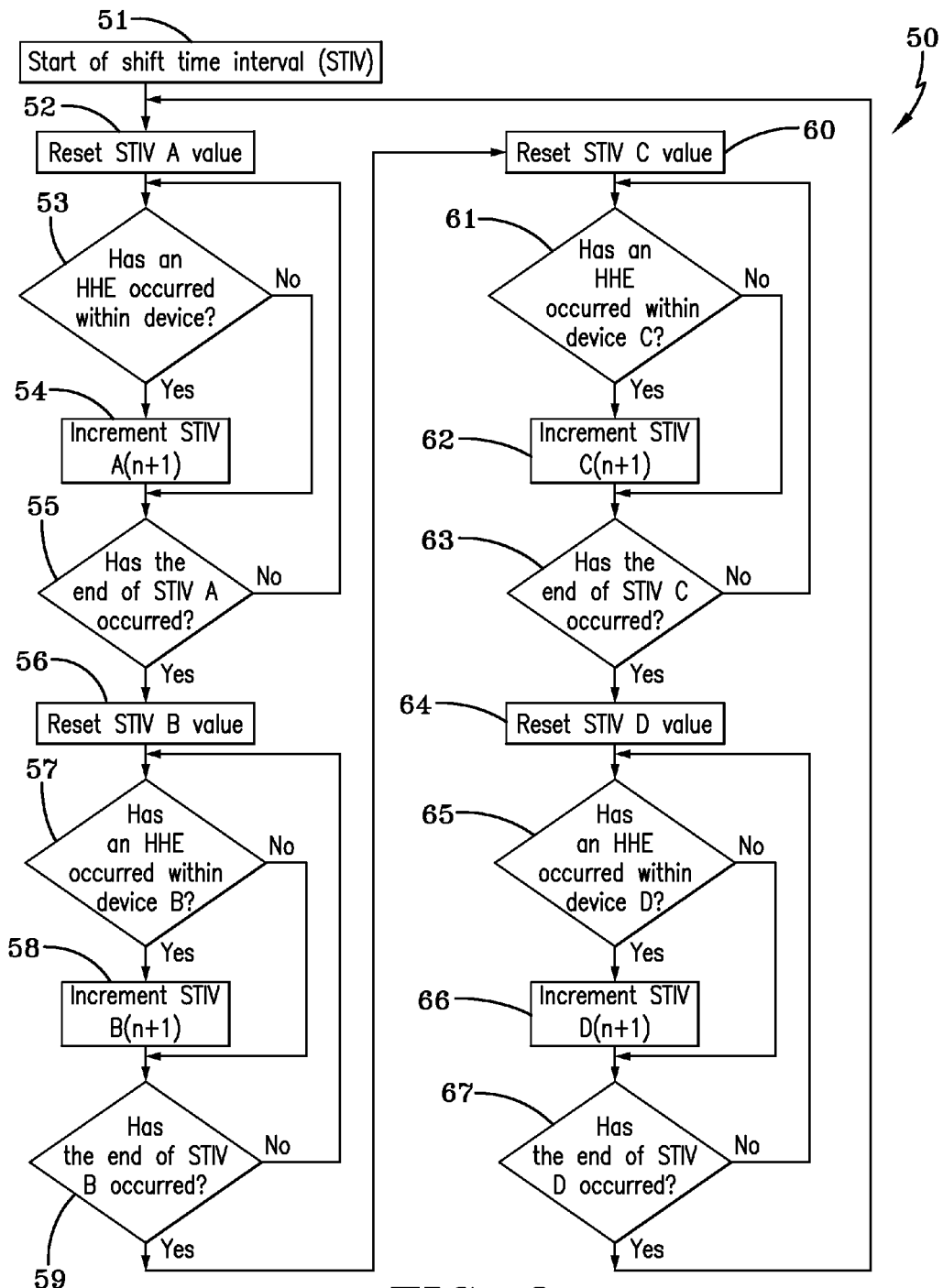
FIG. 3 is a flow diagram of the operational steps taken by the hygiene compliance monitoring system to collect hygiene compliance data within one dispenser in accordance with the concepts of the present invention.

The operational process performed by controller 30 for monitoring compliance and recording the hand hygiene events is designated by the numeral 50 as shown in FIG. 3. The process is shown with respect to a twenty four hour period having four separate shift time intervals to monitor hand hygiene compliance. It should be noted that other minor variations could be accomplished without departing from the scope of the present invention.

The process 50 has a start sequence at step 51, which is representative of the initial operation of controller 30. At step 52, controller 30 stores initial values of zero for the shift time interval value (STIV) of interval A, which is representative of the total number of hand hygiene events recorded within shift time interval A. Each hand hygiene event is representative of one to n number of product dispenses performed in a three second time period. The hand hygiene event is recorded at a maximum of once every three seconds independent of the number of actual product applications to discourage last minute compliance cramming.

At step 53, controller 30 monitors activation switch 25 to determine whether an internal hand hygiene event (HHE) has occurred. When the controller 30 detects an HHE, the controller 30 increments the shift time interval value as shown in step 53 and then proceeds to step 54. If the controller does not detect a HHE, the controller proceeds directly to step 55.

At step 55, the controller 30 determines whether the shift time interval period has ended. If the shift time interval period has not ended, the controller 30 returns to step 53. When the shift time interval period has ended at step 55, the controller 30 proceeds to step 56, and performs similar steps for each shift time interval. Namely, the steps for shift time interval B are designated by steps 56-59, the steps for shift time interval C are designated by steps 60-63, and the steps for shift time interval D are designated by steps 64-67.

Importantly, at the end of step 67, the controller returns to step 52, where the memory of shift time interval A is cleared and written over. This occurs in each of the memory units 31 at the start of each shift time interval, which is shown for steps 56, 60, and 64 for the memory storing the shift time intervals B, C, and D, respectively. For example, a restaurant may associate the shift time intervals for breakfast, lunch, dinner, and late dinner. The memory stored for the breakfast shift is accessible by the manager until the start of the breakfast shift of the following day.

The data acquisition unit 16 may also include an indicator 18 or award indicator, which may comprise an audio speaker and display, such as an LED liquid crystal display to provide an audible and/or visual indication of various states of the data acquisition unit 16 and/or the data transmission unit 14. Alternatively, the indicator 18 may include one or more LED's (light emitting diodes) in which to present a visual indication. Award indicator 18 may use the same shift time interval time used in obtaining compliance data. Award indicator 18 is set to trigger or notify once a random event (i.e. dispense) occurs during an award interval. In other embodiments, multiple awards can be set for each award interval. Award interval may be chosen or set by a company based on its needs. Examples of award intervals are per shift time interval, per day, per week, or per month. Once the award interval is set, interaction with the corresponding dispenser will trigger a random event.

In one aspect, when a random event triggers or actuates the award indicator 18, the indicator generates and audible and/or visual notification, such as illuminating LEDs on the face of the device, indicating an award. The LEDs will remain illuminated for an award illumination time period, which is an amount of time adequate to record the award and corresponding winner. It is contemplated that award illumination time is between one to five minutes. More preferably, the award illumination time is two minutes.

After the award indicator 18 has been triggered (or the total number of awards has been triggered for the designated award interval) the remaining time of the award interval will have to elapse before the next random event (award) can occur.

Figure 4:
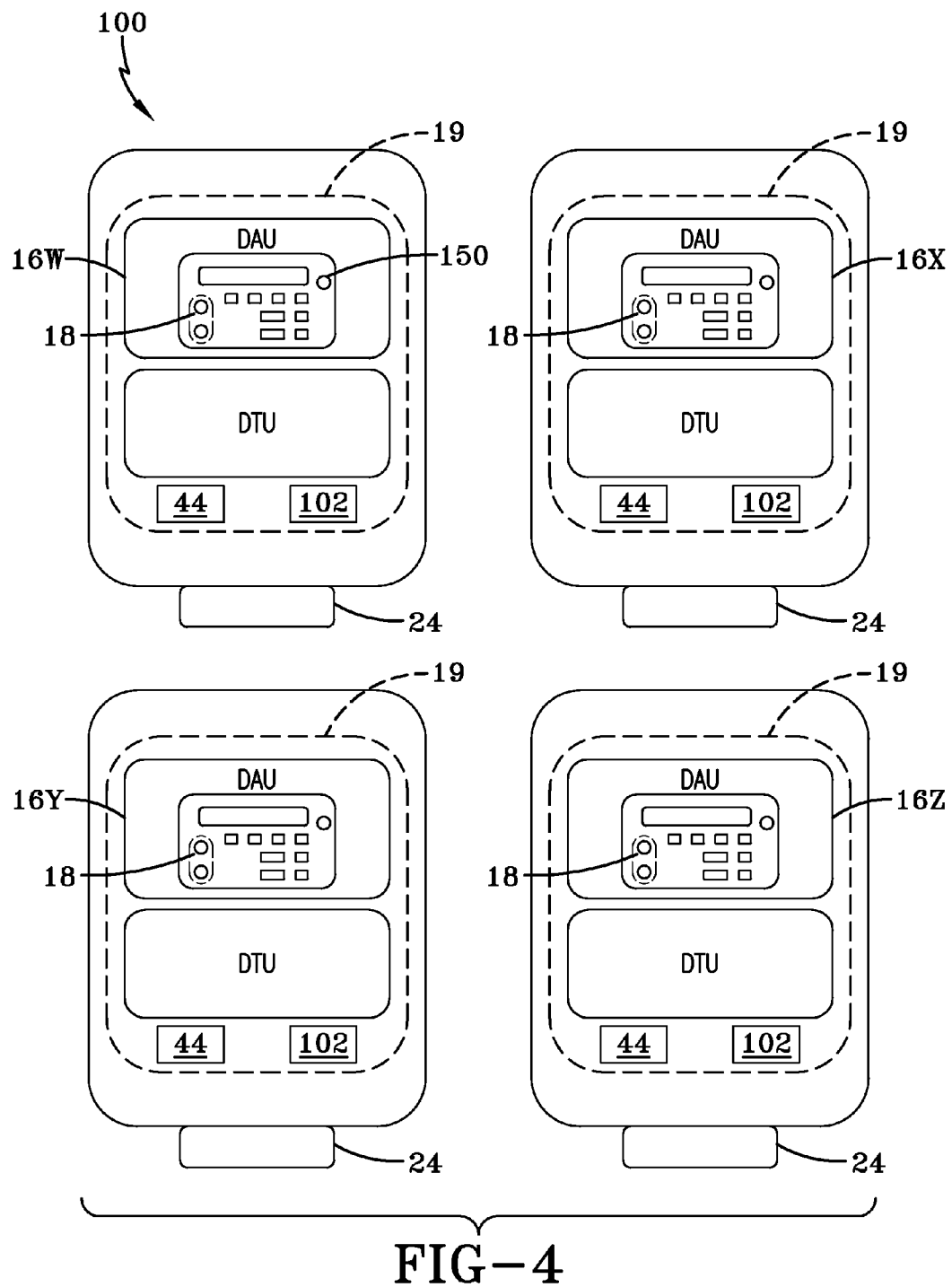
FIG. 4 is a block diagram of a modular hygiene compliance monitoring system that provides a data transmission unit maintained at each dispenser, which transfers collected hygiene compliance data to a data acquisition unit that transmits and receives wireless communication with data acquisition units of dispensers linked in a common functional grouping in accordance with the concepts of the present invention.

A second embodiment of a hygiene compliance monitoring system is generally referred to by the numeral 100, as shown in FIG. 4 of the drawings. The hand hygiene compliance system may be adapted to track usage of multiple dispensers in a functional grouping (multiple dispensers in different locations) and/or each individual dispenser. The system 100 may include similar functions to show total dispenses, total compliance percentage, or no display as the prior embodiment. Similar to the first embodiment the hand hygiene compliance system 100 can be retrofitted to existing dispensers or can be integrally formed within each dispenser. System 100 consists of all of the components; however each dispenser includes a DAU that is in wireless communication with the DAUs of the other dispensers in its functional grouping.

To enable the data acquisition unit (DAU) 16W to wirelessly communicate with the DAUs 16X, 16Y, and 16Z so as to receive hygiene compliance data therefrom, a transceiver 102, such as an RF (radio frequency), IR (infrared), or ultrasound transceiver, is coupled to the data acquisition controller 40. Transceivers 102 provide communication among DAUs 16W, 16X, 16Y, and 16Z that allow for overall system synchronization.

In these embodiments, DAU has additional versatility, because it may track the usage of each individual dispenser or DAU can determine the compliance of the functional grouping as a whole. Below is the functional process to which hand compliance is performed.

The process operates using the same steps as FIG. 3; however additional steps are required with respect to the communication between multiple dispensers. For clarity, each dispenser is designated with its own letter W, X, Y, and Z and each shift time interval is designated by its own letter A, B, C, and D. The process describes in detail the function at dispenser W; however it should be recognized that each dispenser is performing comparable functions.

Figure 5:
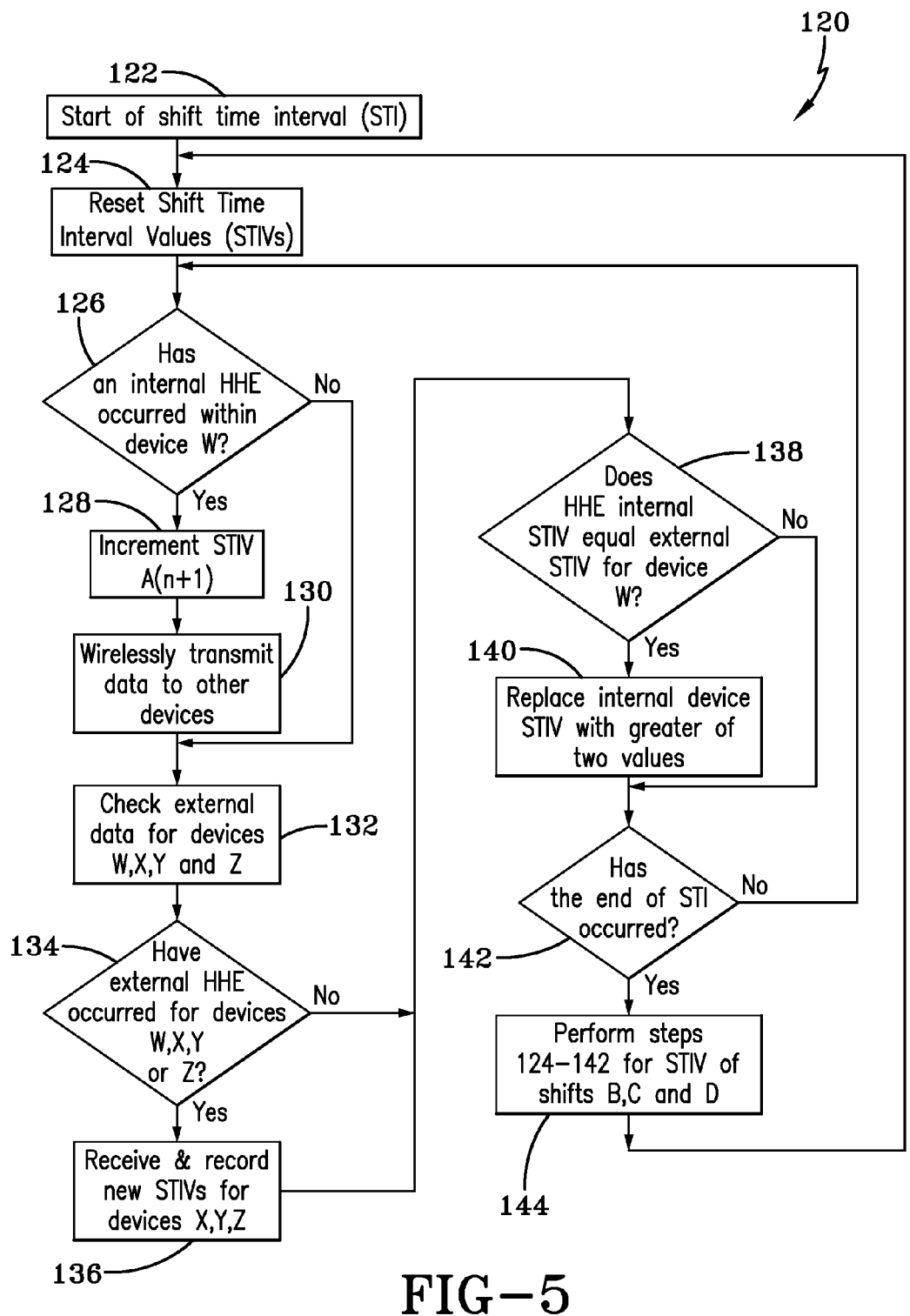
FIG. 5 shows a flow diagram of the operational steps taken to acquire transmitted hygiene compliance data from the data transmission unit and data acquisition unit of one of the dispensers of FIG. 4 in accordance with the concepts of the present invention.

The operational process performed by controller 30 for monitoring compliance and recording the hand hygiene events is designated by the numeral 120 as shown in FIG. 5. The process 120 has a start sequence at step 122, which is representative of the initial operation of controller 30. At step 124, controller 30 stores initial values of zero for the shift time values (STIV) designated for dispensers W, X, Y, and Z. The STIV represents the total number of hygiene events recorded within one shift time interval for each designated device. Each hygiene event is representative of one to n number of product dispenses performed in a three second time period. The hygiene event is recorded at a maximum of once every three seconds independent of the number of actual product applications to discourage last minute compliance cramming.

At step 126, controller 30 monitors an activation switch 25 to determine whether an internal hand hygiene event (HHE) has occurred. When the controller 30 detects an internal HHE, the controller 30 increments the group interval value as shown in step 128 and transmits wireless communication to the other dispensers X, Y and Z at step 130. The controller 30 proceeds to step 132 and reads external STIV data corresponding to devices W-Z. If the controller 30 does not detect an internal HHE at step 126, the controller proceeds directly to step 132 and reads the STIV data of dispensers A-D.

At step 134, controller 30 determines whether an external HHE has occurred for devices X, Y or Z. Meaning, the controller 30 compares the stored STIVs of devices X-Z with the STIVs being transmitted. When the STIVs for devices X-Z differ, the new values are downloaded and stored into device W as shown in step 136. The controller 30 then proceeds to step 138. If the controller 30 does not detect a difference in STIVs for devices X-Z at step 134, the controller 30 proceeds directly to step 138.

At step 138, the controller 30 compares the internal and external STIVs of device W. When the two values are different, the controller 30 selects and stores the greater of the two values for the STIV for interval A at step 140 and proceeds to step 142. If the internal and external STIV of device A are equal at step 138, the controller proceeds directly to step 142.

At step 142, the controller 30 determines whether the shift time interval period has ended. If the shift time interval period has not ended, the controller 30 returns to step 126. Once the shift time interval period ends, the controller 30 proceeds to step 144. The same process (steps 124-142) is performed for each shift time interval B, C, and D.

Importantly, at the end of shift time interval D, the process returns to step 124 where the memory that stores shift time interval A is cleared, and reset to zero. This allows for minimal data storage and provides for confidentiality, because the records are only maintained for a limited period of time before they are written over.

Each DAU 16 may also include the award indicator 18, which provides indication as described in the first embodiment. In the second embodiment described above, hand hygiene compliance system 100 can utilize transceivers 102 to allow DAUs 16W, 16X, 16Y, and 16Z to communicate award indication data to each other. This allows a manager to select award indication to occur on the hand hygiene events of each individual dispenser or for the functional grouping of dispensers.

The data acquisition unit 16 also includes a read dispenser button 150 that is coupled to the data acquisition controller 40. Thus, when the read dispenser button 150 is actuated, the keypad 42 is used to enter a dispenser identification code of a desired dispenser 12 from which to acquire data. Once the dispenser identification code is entered, the data acquisition unit 16 activates the transceiver 102 and sends suitable communication signals to the associated data transmission unit 14 to wirelessly retrieve hygiene compliance data that has been collected thereby.

In addition, the display 45 may also provide feedback with respect to compliance data of each dispenser or the total functional grouping of dispensers for each shift time interval or the total of all four shift time intervals.

Figure 6:
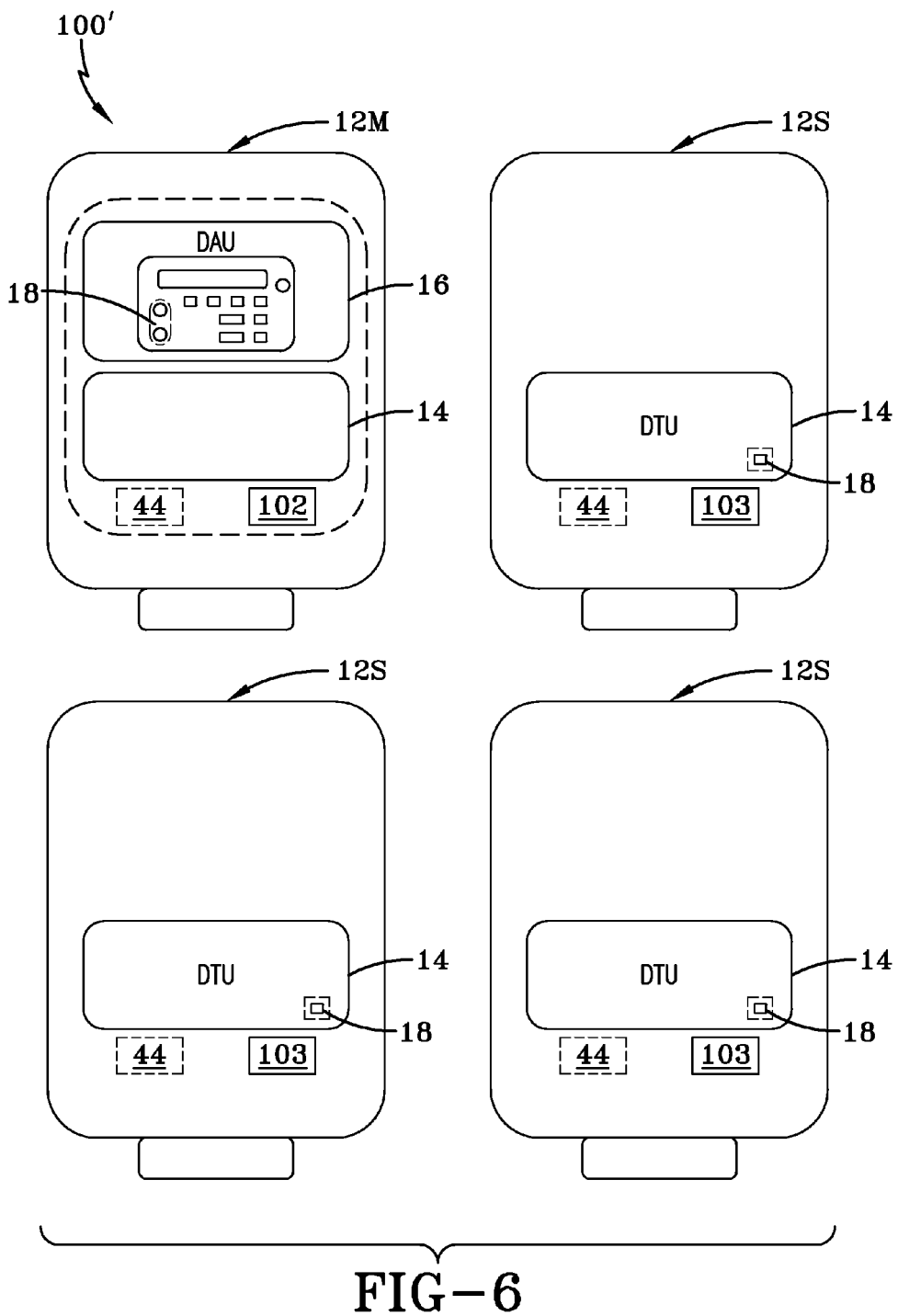
FIG. 6 is a block diagram of a modular hygiene compliance monitoring system that provides a data transmission unit maintained at each dispenser, which transfers collected hygiene data to a single data acquisition unit located on one of the dispensers that are linked in a common functional grouping in accordance with the concepts of the present invention.

In a third embodiment, as shown in FIG. 6, a hygiene compliance monitoring system 100' includes a "master" dispenser 12M along with a plurality of "servant" dispensers 12S. "Master" dispenser 12M that is similar to the dispensers described in the second embodiment. However, transceiver 102 may be replaced by a receiver 102', because "servant" dispensers 12S do not include DAUs 16 as will be further discussed hereinafter. The "master" dispenser performs the steps as shown in FIGS. 3 and 5.

Each "servant" dispenser 12S includes the data transmission unit 14 of the prior embodiments, along with an RF antenna 103 that is in communication with receiver 102' of "master" dispenser 12M. The "servant" dispensers 12S only perform steps 122-130 of FIG. 5. In this embodiment, the compliance manager can monitor the hand hygiene compliance of the functional grouping or each dispenser within the functional grouping from only the "master" dispenser 12M. This embodiment eliminates the need for synchronizing the DAUs 16 as described in the second embodiment.

If award indicator 18 is desired, DAU 16 of "master" dispenser 12M can be identical to that of the second embodiment. Alternatively, and more preferably, the award indicator 18 can also be positioned on each of the "servant" dispensers 12S as well by replacing receiver 102' with transceiver 102" and replacing antennas 103 with servant transceivers 103'. These replacements are necessary to allow the "servant" dispensers 12S to receive the award indication signal from DAU 16 and to trigger the award indicator 18. Since "servant" dispensers 12S do not include a DAU 16, the award indicator can be a separate LED or a component assembled to the DTU 14.

Figure 7:
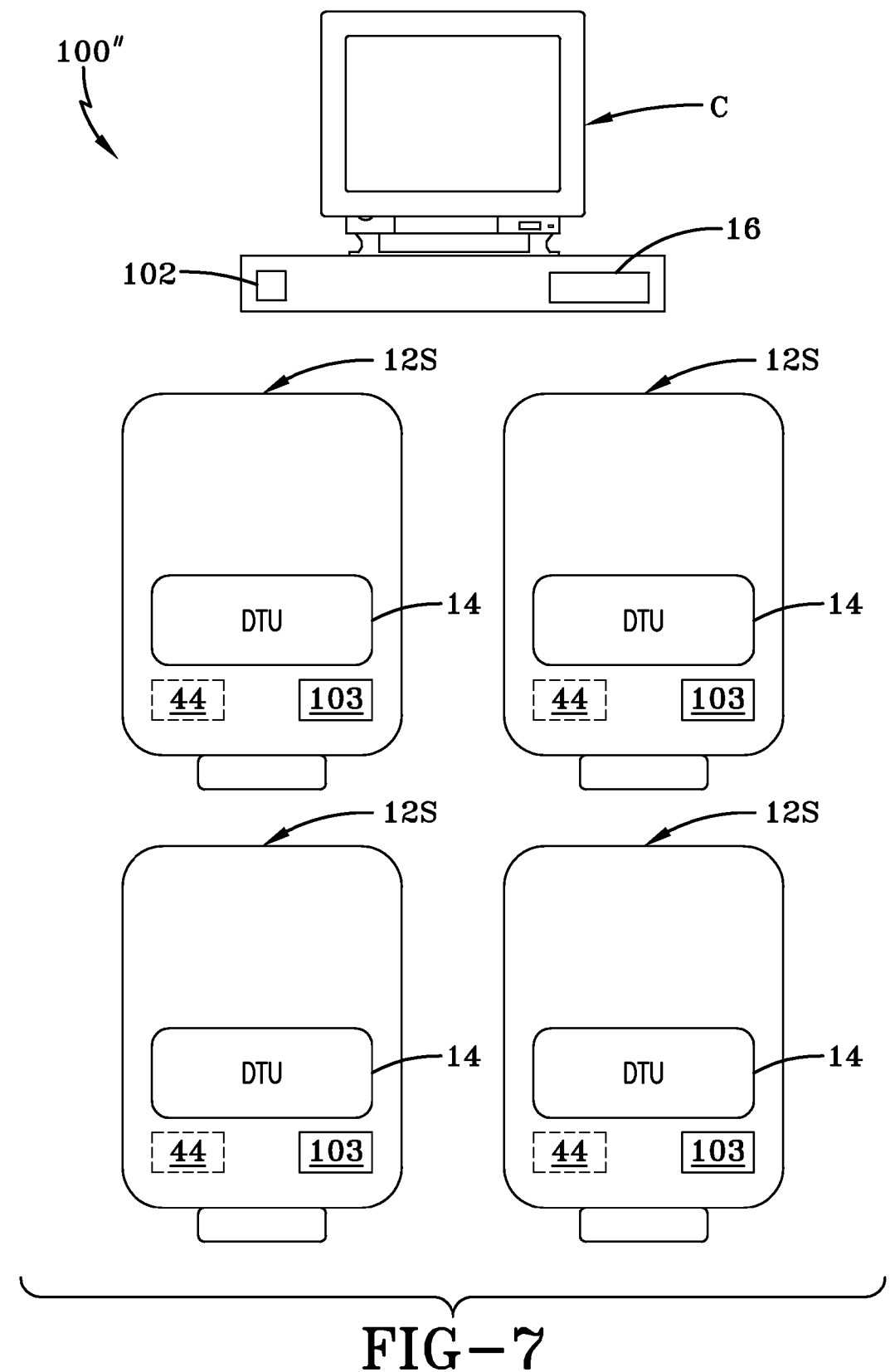
FIG. 7 is a block diagram of a modular hygiene compliance monitoring system that provides a data transmission unit maintained at each dispenser, which transfers collected hygiene data to a single data acquisition unit that is located within a centralized computer and linked in a common functional grouping in accordance with the concepts of the present invention.

In a fourth embodiment, as shown in FIG. 7, the hygiene compliance monitoring system 100" is identical to the third embodiment with the addition of a central monitoring computer C which functions similarly to the "master" dispenser 12M. Computer C includes receiver 102' to gather information from the antennas 103 of the "servant dispensers." In this embodiment, hand hygiene compliance (HHC) rates or the number of accumulated hand hygiene events divided by a target number of hand hygiene events for the Group/STIV will be transmitted to the central monitoring computer at frequent periodic time intervals. The computer will have a stored target value, which is the minimal acceptable HHC rate. When the computer C determines that HHC is less than the acceptable rate, the computer C with internet and/or phone connections will text or notify a manager or assigned individual of the issue.

Figure 8:
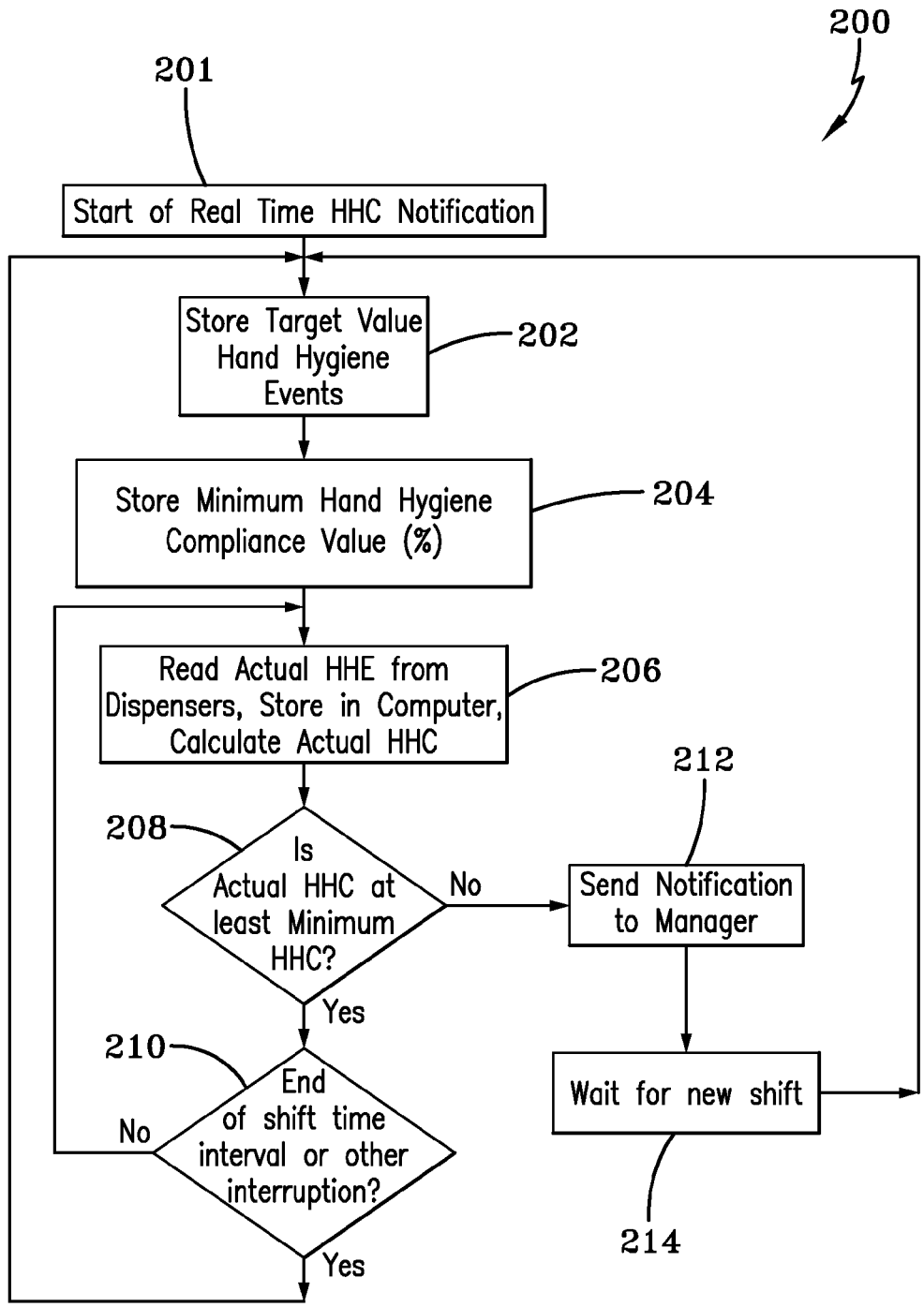
FIG. 8 is flow diagram of the operational steps taken by the hygiene compliance monitoring system to report noncompliance to managers in accordance with the concepts of the present invention.

The operational process performed by Computer C for sending a real time notification is designated by the numeral 200 as shown in FIG. 8. The process 200 begins at an offset (e.g. one hour or certain percentage) from the start of the shift time interval and ends at the same time as the shift time interval. Process 200 has a start sequence at 201, which is representative of the initial operation. It should be noted that the following values can be manually entered by a manager or preprogrammed. At step 202, the target value of hand hygiene events for the given shift time interval is entered. At step 204, the minimum hand hygiene compliance value (HHC) is stored into the computer. The minimum HHC is a percent value of the acceptable rate in which employees comply with hand hygiene and can be based as a function of time and target value of HHEs.

At step 206, the computer calculates the actual HHC by the information it receives from "servant" dispensers 12S. The computer calculates the actual HHC by taking the number of actual HHEs and dividing it by the target number of HHEs that should have occurred within that duration of time (step 202 to current time). At step 208, the computer determines whether actual HHC is greater than the minimum HHC. If actual HHC is greater than the minimum acceptable HHC, the computer proceeds to step 210 where it looks for any other interruptions in the process such as end of shift or manager overwriting the process. If there is no interruption or end of shift time interval, the computer returns to step 206. When there is an interruption or end of shift time interval at step 210, the computer returns to step 202.

When the actual HHC is less than the minimum HHC, the computer C sends a notification to a manager (e.g. text message) as shown in step 212. The computer waits for the end of the shift 214 and then returns to step 202. Alternatively, the computer can utilize a delay (not shown, e.g. one hour) and then return to step 208.

It should be noted that similar functionality for notification of noncompliance may be incorporated within prior embodiments.

Figure 9:
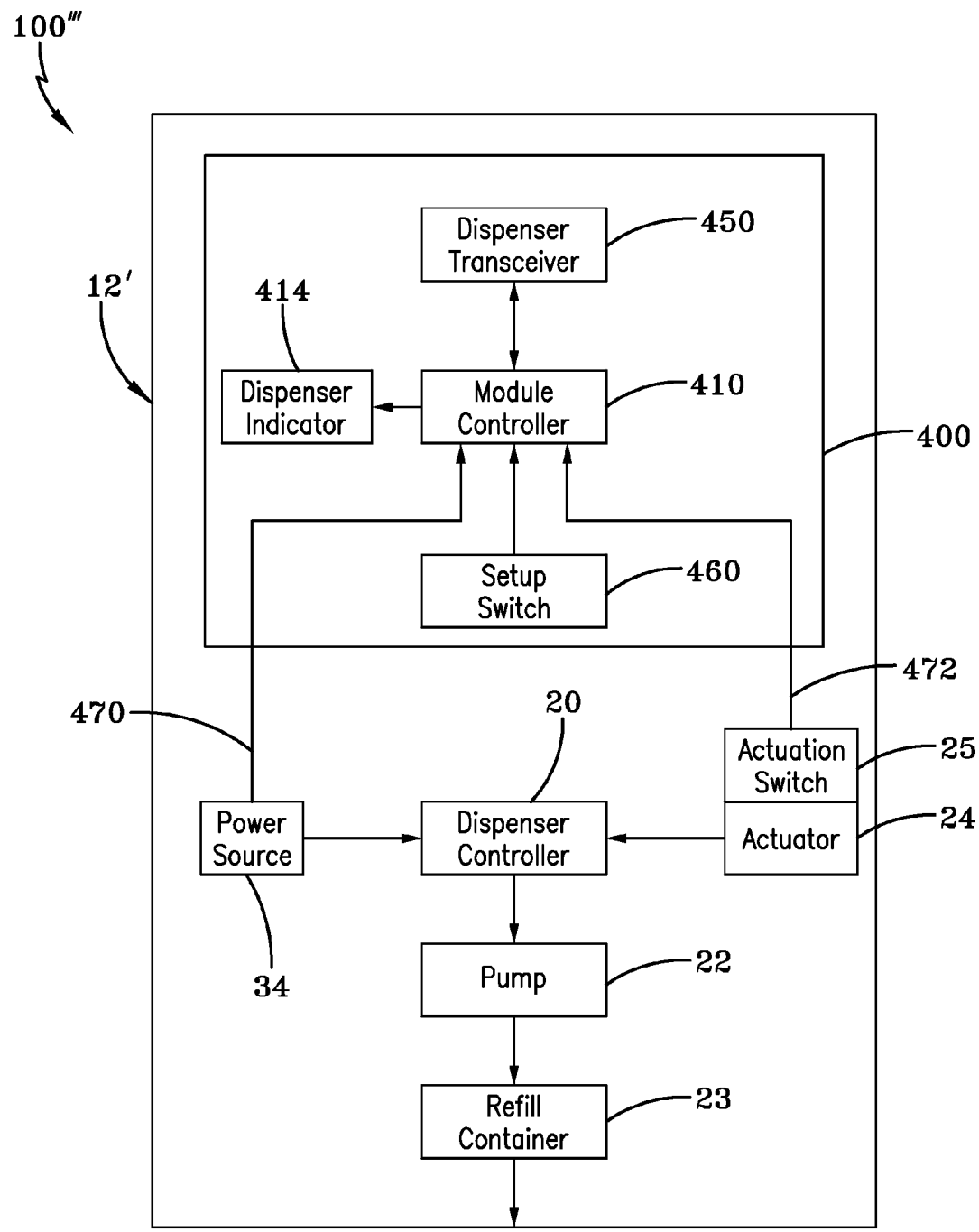
FIG. 9 is a block diagram of the alternative dispenser for use with a dispenser monitoring unit provided by an alternative hygiene compliance monitoring system in accordance with the concepts of the present invention.
Figure 10:
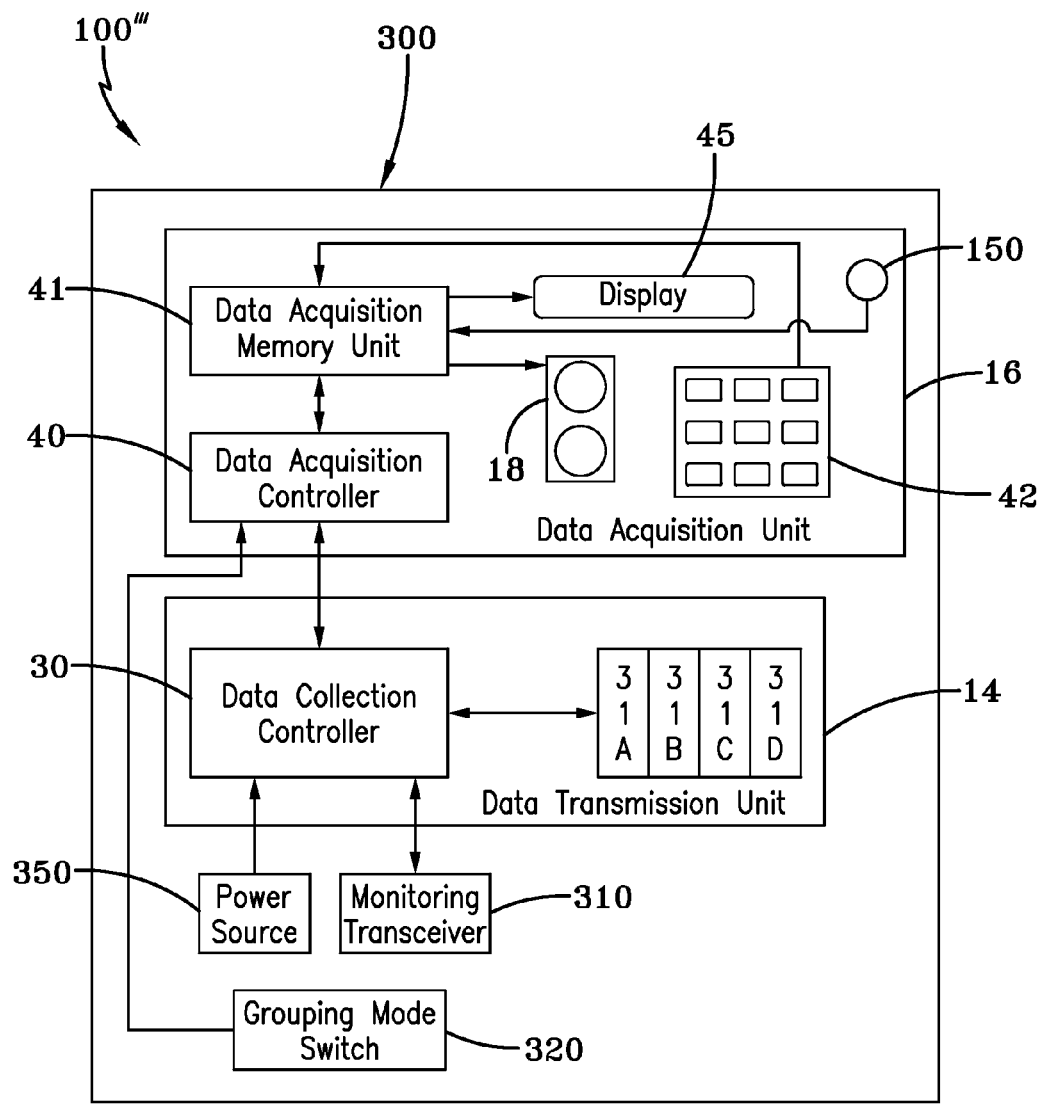
FIG. 10 is a block diagram of the dispenser monitoring unit to monitor a group of alternative dispensers in accordance with the concepts of the present invention.

In a fifth embodiment, as shown in FIGS. 9 and 10, the hygiene compliance monitoring system, referred to by numeral 100' includes a dispenser monitoring unit 300 that is used to associate one or more dispensers 12' together as a functional group so that the hygiene compliance of the entire functional group can be monitored in a manner to be discussed. It should be appreciated that the dispenser 12', shown in FIG. 9, is structurally equivalent to dispenser 12 but only includes the dispenser controller 20, the pump 22, the refill container 23, the actuator 24, the activation switch 25, and the power source 34, previously discussed with regard to FIG. 2.

The dispenser monitoring unit 300 shown in FIG. 10 includes the data transmission unit 14 and the data acquisition unit 16 previously discussed, while a monitoring transceiver 310 coupled to the data collection controller 30 enables communication with the dispensers 12'. However it should be appreciated that the functions of the data acquisition controller 40 and the data collection controller 30 may be combined into a single monitoring controller. The dispenser monitoring unit 300 also includes a grouping mode switch 320 that is coupled to the data acquisition controller 40 that when actuated, places the dispenser monitoring unit 300 into a grouping or naming mode, which will be discussed in detail below. The grouping mode switch 320 may comprise a magnetic switch, such that when a complementary magnetic key is placed in proximity thereto, the monitoring unit 300 is caused to enter the grouping mode. For example, the grouping mode switch 320 may comprise a reed or hall-effect switch or may comprise any other suitable secure switch, such as a mechanical keyed switch that requires a corresponding key to mechanically actuate the grouping mode switch 320 in order to enter the grouping mode. It should also be appreciated that the mode switch 320 may be located on the dispenser monitoring unit 300 so that it is hidden or obscured from the view of users to prevent unauthorized access. It should also be appreciated that in lieu of the grouping mode switch 320, the grouping mode may be entered at the dispenser monitoring unit 300 by inputting a predetermined numeric and/or alphabetic code at the keypad 42. As such, making the mode switch 320 a keyed switch, as well as hiding its location, or using a code ensures that only authorized personnel are permitted to enter the grouping mode. The dispenser monitoring unit 300 also includes a power source 350 that is coupled to the data collection controller 30, which serves to energize the components of the dispenser monitoring unit 300. In one aspect, the power source 350 may comprise any suitable source of power, such as a battery or an A.C. (alternating current) mains power source, such as that provided by a standard electrical wall outlet. As such, the dispenser monitoring unit 300 provides the clock, memory, target level, and other components that have been previously discussed as being part of the dispenser 12 in the other embodiments of the hygiene compliance monitoring system. As a result a reduced number of components are added to the dispenser 12', thus reducing cost, while still enabling the dispenser monitoring unit 300 to generate hygiene compliance data that is based on the number of hand hygiene events generated by one or more dispensers 12'.

In order to acquire hygiene compliance data and to invoke various other functions at the dispenser 12', the hygiene compliance system 100''' also includes a dispenser module 400 that is configured to be retrofit to the dispenser 12', shown in FIG. 9. However, it should be appreciated that the dispenser module 400 may be made integral with the components of the dispenser 12' at the time of manufacture. The dispenser module 400 includes a module or dispenser controller 410 that includes the necessary hardware and/or software to perform the functions to be discussed. It should also be appreciated that the module or dispenser controller 410 may include an identification code or serial number that uniquely identifies each module 400 and ultimately each dispenser 12' to which it is coupled. The module controller 410 is coupled to a dispenser indicator 414, which may generate any desired audio and/or video notification. In one aspect, the dispenser indicator 414 may comprise an LCD display or one or more LEDs (light emitting diodes) and/or an audio speaker. The module controller 410 is also coupled to a dispenser transceiver 450 that is configured to communicate various data, such as hand hygiene event data, group code data, and dispenser identification code data to the monitoring transceiver 310 of the dispenser monitoring unit 300. The dispenser module 400 also includes the setup switch 460 that is coupled to the module controller 410 to enable the dispenser 12' to be placed into a grouping mode so as to allow the dispenser 12' to be added or otherwise associated as part of a functional group of one or more dispensers (i.e. one or more dispensers in various locations) that each communicate directly with the dispenser monitoring unit 300. It should also be appreciated that the setup switch 460 may be hidden from plain view of users of the dispenser 12' and otherwise made secure in a manner equivalent to that of the grouping mode switch 320. In order to power the dispenser module 400, the module controller 410 is coupled to the power source 34 provided by the dispenser 12' and to the activation switch 25 provided by the dispenser 12' via respective connection terminals 470 and 472. As such, the connection terminals 470 and 472 allow the dispenser module 400 to be easily retrofit to any existing dispensers 12' that lack hygiene compliance functionality. However, as previously discussed, the dispenser module 400 may be made integral with the dispenser 12' without the need of the terminals 470, 472. Alternatively, the dispenser module 400 may not include the dispenser controller 410, such that the terminals 470 and 472 are coupled directly to the dispenser transceiver 450. Similarly, the dispenser indicator 414 may also be coupled directly to the dispenser transceiver 450 in the event that the dispenser controller 410 is eliminated from the dispenser module 400. In other words, in an alternative embodiment the dispenser module 400 may be configured to include only the dispenser transceiver 450, and may optionally include one or more of the dispenser indicator 414, and setup switch 460.

Thus, the grouping mode allows one or more dispensers 12', which may be located in various areas of a facility, to be identified as part of a single functional group so that hand hygiene events occurring at the grouped dispensers 12' can be monitored together in the aggregate by the dispenser monitoring unit 300. That is, the total number of hand hygiene events that have occurred at all of the grouped dispensers 12' during a given time segments or shift time intervals can be analyzed as a combined summation at the dispenser monitoring unit 300, in the manner previously discussed with regard to other embodiments of the hygiene compliance system.

Figure 11:
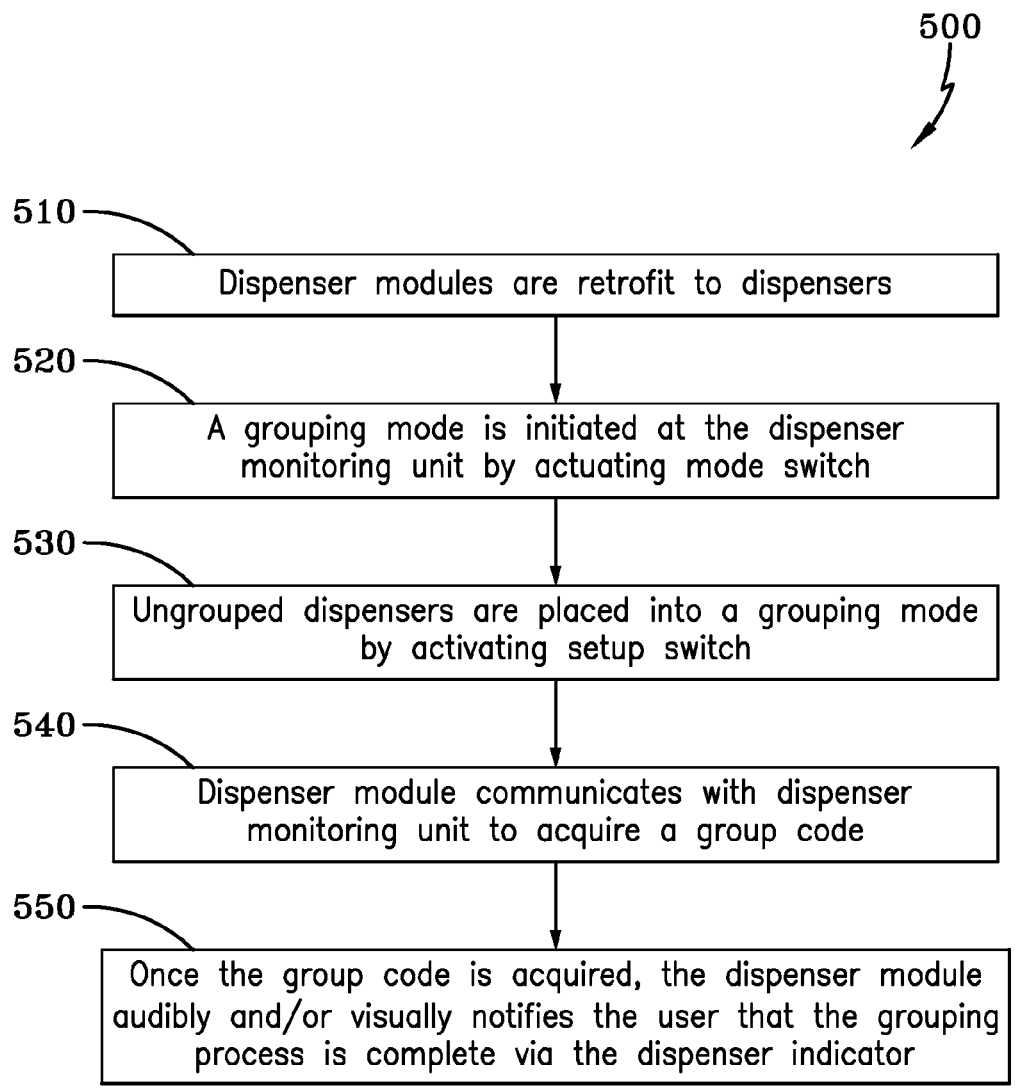
FIG. 11 is a flow diagram showing the operational steps taken during a grouping process carried out between the dispenser monitoring unit and one or more alternative dispensers in accordance with the concepts of the present invention.

As such, the operational steps taken by the dispenser monitoring unit 300 and the dispenser 12' to associate one or more dispensers 12' together as a functional group are generally referred to by the numeral 500, are shown in FIG. 11. Initially at step 510, the dispenser modules 400 are retrofit to each dispenser 12' that is desired to be included in a group. However, it should be appreciated that if the components of the dispenser module 400 are made integral with the dispenser 12', step 510 is no longer necessary. At step 520, the grouping mode is initiated at the dispenser monitoring unit 300 by actuating the mode switch 320. In one aspect, the user may select a specific group code to be used during the grouping process by entering it via the keypad 42 of the dispenser monitoring unit 300. Next, the ungrouped dispenser 12' that is desired to be added to a group is placed into a grouping mode by actuating the setup switch 460, as indicated at step 530. Once both the dispenser monitoring unit 300 and the dispenser 12' that is desired to be part of a group are placed in the grouping mode, the dispenser transceiver 450 of the dispenser 12' communicates with the monitoring transceiver 310 of the dispenser monitoring unit 300 to acquire a group code, such as group name or group identification code that is to be assigned to the dispenser 12' by the dispenser monitoring unit 300, as indicated at step 540. Furthermore, step 540 may be repeated for each additional dispenser 12' being added to a given functional group. It should also be appreciated that the in order to carry out step 540, the dispenser 12' may communicate its associated unique identification code or serial number to the dispenser monitoring unit 300 to identify which specific dispensers 12' are to be part of a group and associated with a give group code. It should be appreciated that the group name or identification code may comprise any code, such as a numeric and/or alphabetic code. That is, the dispenser monitoring unit 300 may identify each dispenser 12' by its unique serial number that is stored at the module controller 410, which is communicated to the dispenser monitoring unit 300 during the grouping process. Finally, once the group code is acquired by the dispenser 12', the dispenser indicator 414, at step 550, audibly and/or visually indicates that the grouping process has been completed.

Figure 12:
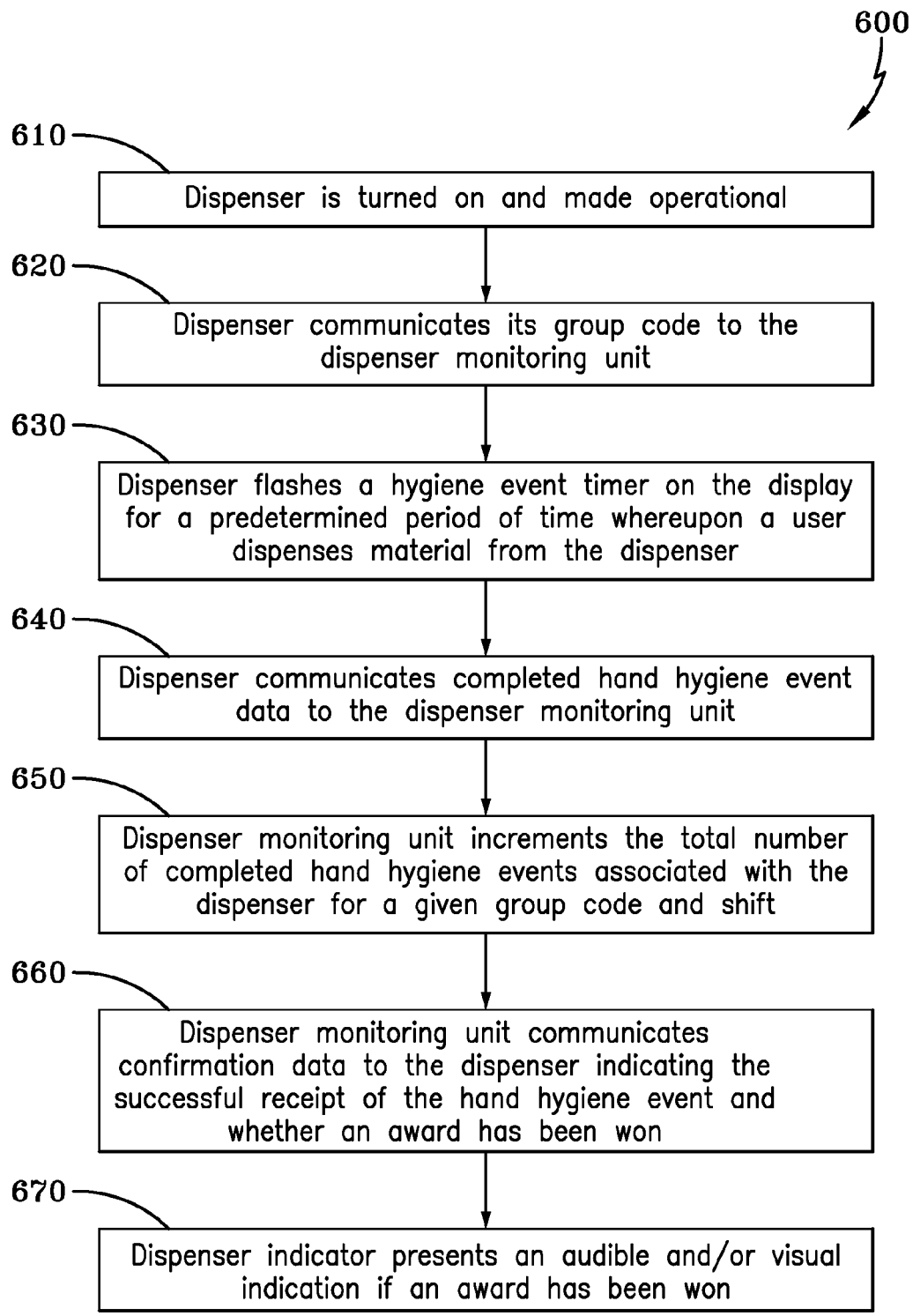
FIG. 12 is a flow diagram showing the operational steps taken during the operation of the dispenser monitoring unit and one or more alternative dispensers in accordance with the concepts of the present invention.

Once the grouping process has been performed to associate one or more dispensers 12' with the dispenser monitoring unit 300 as a functional group, the dispensers 12' are able to be placed into use, so as to carry out the operational steps generally referred to by the numeral 600, as shown in FIG. 12. Initially, at step 610 the dispenser is turned ON and made operational. Next, the dispenser transceiver 450 of the dispenser module 400 associated with the dispenser 12' communicates its group name or code to the dispenser monitoring unit 300, as indicated at step 620. Continuing to step 630, the dispenser 12' flashes the hygiene event timer that is shown on the display 45 for a predetermined period of time, such as 30 seconds for example, whereupon the user of the dispenser 12' is permitted to dispense material from the dispenser 12' into his or her hands. Upon the completion of a hand hygiene event in which material from the refill container 23 has been dispensed from the dispenser 12', the dispenser module 400 communicates the completed hand hygiene event to the monitoring transceiver 310 of the dispenser monitoring unit 300, as indicated at step 640. Upon receipt of the hand hygiene event data, the process 600 continues to step 650 where the data collection controller 30 of the dispenser monitoring unit 300 increments a shift count value that identifies the total number of hand hygiene events that have been completed at all of the dispensers 12' that are associated with the current group and shift being monitored. After step 650 has been completed, the dispenser monitoring unit 300 communicates confirmation data back to the particular dispenser 12' that was used, so as to indicate that the hand hygiene event data sent by the dispenser 12' was successfully received by the dispenser monitoring unit 300, as indicated at step 660. Also at step 660, the dispenser monitoring unit 300 may communicate award data to one or more designated dispensers 12' to indicate that an award, as previously discussed, has been won. Upon the expiration of the event timer at step 660, the dispenser indicator 414 presents an audible and/or visual indication if an award has been won, as indicated at step 670.

It should also be appreciated that the data acquisition unit 16 of the dispenser monitoring unit 300 may include the read dispenser button 150 that is coupled to the data acquisition controller 40. Thus, when the read dispenser button 150 is actuated, the keypad 42 is used to enter an individual dispenser identification code of a desired dispenser 12' or a desired group code to view via the display 45 hygiene compliance data that is associated with the group of dispensers 12'. In addition, the display 45 may also provide feedback with respect to hand hygiene events and associated compliance data of each dispenser 12' or the for the total functional grouping of dispensers associated with the group code of one or more shift time intervals, as well as, the total of all the shift time intervals.

It will, therefore, be appreciated that one advantage of one or more embodiments of the present invention is that a hygiene event monitoring system provides a simple and user-friendly system in which to monitor activity at a dispenser and overall hand hygiene compliance in real time.

Although the present invention has been described in considerable detail with reference to certain embodiments, other embodiments are possible.

Therefore, the spirit and scope of the appended claims should not be limited to the description of the embodiments contained herein.

What is claimed is:

1. A hygiene compliance monitoring system for a dispenser maintaining material to be dispensed, the hygiene compliance monitor system comprising:
    a controller having at least one shift time interval and a target value of hand hygiene events corresponding to said at least one shift time interval; and
    an activation switch that communicates an at least one actual hand hygiene event data to a memory unit, said memory unit having at least one memory bank corresponding to said at least one shift time interval, such that said controller compares the at least one actual hand hygiene event data to the target value of hand hygiene events;
    wherein the memory unit has at least a first memory bank and a second memory bank, wherein said first memory bank corresponds to a first shift time interval and said second memory bank corresponds to a second shift time interval, and further wherein said first and second memory banks operate in a cycle wherein each of said first and said second shift time intervals has a start time and an end time, and further wherein said start time of said second shift time interval immediately follows said end time of said first shift time interval.

2. The hygiene compliance monitoring system of claim 1, wherein the hygiene compliance monitor system includes a data acquisition unit having a display and a keypad.

3. The hygiene compliance monitoring system of claim 2, wherein the hygiene compliance monitor system includes a manager's key to enable operation of said keypad and said display.

4. The hygiene compliance monitoring system of claim 3, wherein said manager's key is a personal identification number that can be entered on said keypad.

5. The hygiene compliance monitoring system of claim 4, wherein said keypad allows the display to be adjusted from no display to information regarding hand hygiene compliance data.

6. The hygiene compliance monitoring system of claim 1, wherein a number of said memory banks is equal to a number of said shift time intervals.

7. The hygiene compliance monitoring system of claim 1, wherein said target value is provided as a function of time.

8. The hygiene compliance monitoring system of claim 1, wherein said target value is set to a fixed number.

9. A hygiene compliance monitoring system for a dispenser maintaining material to be dispensed, the hygiene compliance monitor system comprising:
    a controller having at least one shift time interval and a target value of hand hygiene events corresponding to said at least one shift time interval;
    an activation switch that communicates an at least one actual hand hygiene event data to a memory unit, said memory unit having at least one memory bank corresponding to said at least one shift time interval, such that said controller compares the at least one actual hand hygiene event data to the target value of hand hygiene events;
    an award indicator; and
    a second controller associated with a second memory unit, said second controller being associated with said controller and providing a random event over a preselected reward time period, wherein said random event triggers said award indicator and can only happen once per said shift time interval.

10. A hygiene compliance monitoring system for a dispenser maintaining material to be dispensed, the hygiene compliance monitor system comprising:
    a controller having at least one shift time interval and a target value of hand hygiene events corresponding to said at least one shift time interval;
    an activation switch that communicates an at least one actual hand hygiene event data to a memory unit, said memory unit having at least one memory bank corresponding to said at least one shift time interval, such that said controller compares the at least one actual hand hygiene event data to the target value of hand hygiene events; and
    a transceiver in communication with said controller, such that said transceiver relays said actual hand hygiene events to other dispensers, and receives other dispenser hygiene event data from said other dispensers, and wherein said controller sums the actual hand hygiene events and the other dispenser hygiene event data;
    wherein each dispenser has an award indicator and a second controller associated with a second memory unit, said second controller is also associated with said controller and provides a random event over a preselected reward time period, wherein said random event triggers at least one of said award indicators and can only happen once per said shift time interval.

11. The hygiene compliance monitoring system of claim 10, wherein the target value corresponds to the sum of said dispenser target value and other dispensers target data.

12. A hygiene compliance monitoring system for a functional grouping of dispensers wherein said functional grouping of dispensers includes more than one dispenser maintaining material to be dispensed, said hygiene compliance monitor comprising:

a dispenser controller that is coupled to an actuator of each dispenser within said functional grouping of dispensers, wherein said actuator initiates the dispensation of material from the dispenser when actuated;

a data transmission unit adapted to be coupled to said dispenser controller of each dispenser within said functional grouping of dispensers, said data transmission unit including a data collection memory unit and an internal clock in synchronization with the other dispensers of said functional grouping of dispensers, said memory unit having at least one memory bank for receiving data, said data transmission unit generating a series of successive shift time intervals wherein said shift time intervals are periods to which said at least one memory bank stores data from said internal clock, said shift time intervals being repeated in a sequence, and each of said at least one memory bank is deleted at the start of each said shift time interval; and at least one data acquisition unit configured to set said clock and being further configured to receive at least one piece of data of said at least one actuation.

13. The hygiene compliance monitor of claim 12, wherein there is only one said data acquisition unit.

14. The hygiene compliance monitor of claim 13, wherein the one said data acquisition unit is affixed to one of the dispensers of the functional grouping.

15. The hygiene compliance monitor of claim 13, wherein the one said data acquisition unit is contained within a computer.

16. A method of hygiene compliance monitoring, comprising:

providing a data transmission unit maintained by a dispenser, said dispenser including an actuator to initiate the dispensation of material from a refill container and a plurality of memory banks, wherein said data transmission unit performs the steps of:

storing a target value of dispensations;

generating a plurality of shift time intervals of a predetermined duration that repeat in a sequence, wherein each said shift time interval corresponds to each said memory bank;

clearing the memory bank at the beginning of each said shift time interval;

monitoring the engagement of said actuator; and storing the number of engagements for each shift time interval into each memory bank; and providing a data acquisition unit having a display and keypad, said data acquisition unit configured to communicate with said data transmission unit, and wherein said data transmission unit transfers the number of engagements and associated shift time intervals to the display of the data acquisition unit.

17. The method of claim 16 further comprising:

providing an award indicator having a indicator controller and indicator memory in said data acquisition unit, wherein said award indicator:

stores an alarm to provide an indication;

provides that an actuation creates a random event;

allows a user to select a time segment to which said alarm shall occur;

generates said indication at the award indicator when said random event occurs; and resets said alarm at the end of said time segment for next random event.

18. The method of claim 16, wherein said step of providing a data transmission unit includes providing multiple data transmission units.

19. A dispenser monitoring unit to monitor hand hygiene compliance of at least one dispenser that transmits a hand hygiene event each time an actuator is engaged to dispense material therefrom, the dispenser monitoring unit comprising:

a monitoring controller;

a monitoring transceiver coupled to said monitoring controller to receive the hand hygiene events transmitted from the at least one dispenser; and a data collection memory unit and an internal clock each coupled to said monitoring controller, said memory unit having at least one memory bank for receiving at least one hand hygiene event, said monitoring controller generating a series of successive shift time intervals, wherein said shift time intervals are periods to which said at least one memory bank stores data from said internal clock, said shift time intervals being repeated in a sequence, and each of said at least one memory bank is deleted at the start of each said shift time interval.

20. The dispenser monitoring unit of claim 19, wherein said monitoring controller sums the hand hygiene events received from the dispensers.

21. The dispenser monitoring unit of claim 20, wherein said monitoring controller is programmed with a target value of hand hygiene events, said monitoring controller comparing said sum and said target value to generate hygiene compliance data.

22. The dispenser monitoring unit of claim 21, further comprising:

a display coupled to said monitoring controller to present said hygiene compliance data.

23. The dispenser monitoring unit of claim 19, wherein said monitoring controller is configured to set said clock.

24. The dispenser monitoring unit of claim 19 further comprising:

a grouping mode switch coupled to said monitoring controller, wherein when said grouping mode switch is activated, said monitoring transceiver acquires a dispenser identification code from each dispenser and associates each dispenser identification code with a group code generated by said monitoring controller.

25. The dispenser monitoring unit of claim 19, wherein said monitoring controller provides a random event over a preselected reward time period, such that said random event triggers a dispenser indicator provided by at least one dispenser.

\* \* \* \* \*